US006566403B1

(12) United States Patent
Michelotti et al.

(10) Patent No.: US 6,566,403 B1
(45) Date of Patent: May 20, 2003

(54) N-ACETONYLBENZAMIDE FUNGICIDES

(75) Inventors: Enrique Luis Michelotti, Fort Washington, PA (US); David Hamilton Young, Ambler, PA (US); Thomas Anthony McLaughlin, Penndel, PA (US)

(73) Assignee: Dow AgroSciences LLC, Indianapolis, IN (US)

( * ) Notice: Subject to any disclaimer, the term of this patent is extended or adjusted under 35 U.S.C. 154(b) by 894 days.

(21) Appl. No.: 08/874,463

(22) Filed: Jun. 16, 1997

(51) Int. Cl.[7] ............. A61K 31/166; A01N 47/46; C07C 233/84; C07D 213/30
(52) U.S. Cl. ............. 514/617; 564/183; 564/161; 564/166; 564/176; 558/14; 558/17; 558/392; 558/415; 546/316; 546/317; 514/514; 514/522; 514/619
(58) Field of Search .............. 558/14, 17, 392, 558/415; 564/161, 166, 176, 183; 514/514, 522, 617, 619; 546/317, 316

(56) References Cited

U.S. PATENT DOCUMENTS

| 4,822,902 A | * | 4/1989 | Carley | 558/14 |
| 5,304,572 A | * | 4/1994 | Michelotti | 514/514 |

FOREIGN PATENT DOCUMENTS

| EP | 0170498 A2 | 2/1986 |
| EP | 0173453 A1 | 3/1986 |

OTHER PUBLICATIONS

Gordon, E.M. et al., On the Facile Dehydrohalogenation of Amino Acid Derived Chloromethyl Ketones, *Tetrahedron Letters*, vol. 25, No. 31, pp. 3277–3280, 1984.

* cited by examiner

*Primary Examiner*—Charanjit S. Aulakh
(74) *Attorney, Agent, or Firm*—Thomas D. Rogerson

(57) ABSTRACT

This invention relates to new compositions comprising predominantly one enantiomer of an N-acetonylbenzamide fungicide, methods of preparing N-acetonylbenzamides, and their use as fungicides.

11 Claims, No Drawings

N-ACETONYLBENZAMIDE FUNGICIDES

This invention relates to new compositions of N-acetonylbenzamide fungicides, methods of preparing the N-acetonylbenzamides, and their use as fungicides.

N-acetonylbenzamide fungicides are known, see, e. g., U. S. Pat. Nos. 5,254,584 and 5,304,572. One advantage of these known fungicides is that they have high fungicidal activity. Such compounds are particularly advantageous because their high activity allows them to be used at low application rates. However, there is always a need for fungicidal compounds of even higher activity. This results in lower use rates and, therefore, less environmental contamination.

We have discovered that with certain N-acetonylbenzamide fungicides which contain an assymetric carbon atom, the fungicidal activity results primarily from one enantiomer. Thus, fungicidal compositions containing only the active enantiomer provide higher fungicidal activity than compositions containing both enantiomers, when used at the same use rate.

This invention provides compositions, comprising:
a. a compound of formula I, with the stereochemistry depicted:

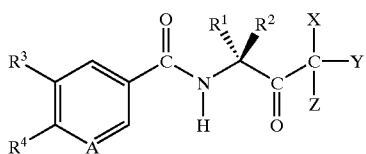

wherein:
1. A is selected from N and C-$R^5$;
2. $R^1$ and $R^2$ are different and are independently selected from H, ($C_1$–$C_6$)alkyl, ($C_2$–$C_6$)alkenyl, ($C_2$–$C_6$)alkynyl, and halo($C_1$–$C_6$)alkyl and $R^2$ is stereochemically larger than $R^1$;
3. $R^3$, $R^4$, and $R^5$ are independently selected from H, halo, ($C_1$–$C_6$)alkyl, ($C_2$–$C_6$)alkenyl, ($C_2$–$C_6$)alkynyl, halo ($C_1$–$C_6$)alkyl, (Cl-C6)alkoxy, halo($C_1$–$C_6$)alkoxy, cyano, nitro, —$CR^6$=$NOR^7$, —$NR^8R^9$, —$CONR^{10}R^{11}$, and —NH—CO—$OR^{12}$ wherein $R^6$ is selected from H, ($C_1$–$C_6$)alkyl, ($C_2$-C6)alkenyl, and ($C_2$–$C_6$)alkynyl, $R^7$ is selected from H, ($C_1$–$C_6$)alkyl, ($C_2$–$C_6$)alkenyl, ($C_2$–$C_6$)alkynyl, and ($C_1$–$C_6$)alkylcarbonyl, $R^8$ and $R^9$ are independently selected from H, ($C_1$–$C_6$)alkyl, and ($C_1$–$C_6$)alkylcarbonyl, $R^{10}$ and $R^{11}$ are independently selected from H and ($C_1$–$C_6$)alkyl; and $R^{12}$ is selected from H, ($C_1$ –$C_6$)alkyl, ($C_2$–$C_6$) alkenyl, and ($C_2$–$C_6$) alkynyl; and
4. X, Y, and Z are independently selected from H, halo, cyano, thiocyano, isothiocyano, and ($C_1$–$C_4$) alkylsulfonyloxy; provided that X, Y, and Z are not all H; and
b. an agronomically acceptable carrier;

wherein the composition is predominantly free of the compound of formula I wherein $R^1$ is stereochemically larger than $R^2$;.

The term "halo" means chloro, fluoro, bromo, or iodo. The terms "alkyl" and "alkenyl" include straight-chain, branched-chain, and cycloalkyl and alkenyl groups. The term "alkynyl" includes straight-chain and branched-chain alkynyl groups. The term "alkoxy" includes as the alkyl portion straight-chain, branched-chain, and cyclic alkyl and alkenyl groups. The term "halo" preceeding any one of alkyl, alkenyl, alkynyl, or alkoxy means that one or more of the hydrogens of the group is substituted with a halogen.

The term "stereochemically larger" means the group in question is more space-filling than the group to which it is being compared. When the $R^1$ and $R^2$ groups in formula I contain only carbon and hydrogen atoms, since $R^2$ is the stereochemically larger group, the stereochemistry about the atom to which the $R^1$ and $R^2$ groups are attached will take on an "S" configuration. That is, the compound of formula I is designated as the S enantiomer. Throughout this application, the term "S enantiomer" means that the four groups on the carbon to which $R^1$ and $R^2$ are attached, when ranked according to the set of sequence rules of the Cahn-Ingold-Prelog system (*Angew. Chem. Int. Ed. Engl.* 5, 385–415(1966)), define the carbon as having an S configuration. The term "R enantiomer" means that the four groups form an R configuration. The term "predominantly free" means that the ratio of enantiomers is greater than 3:1, preferably greater than 5:1, more preferably greater than 10:1, and most preferably greater than 100:1.

Because of their high fungicidal activity preferred compounds are those of formula I wherein: $R^3$ is selected from halo, cyano, nitro, and —CH=NOCH3; $R^4$ is selected from H, halo, cyano, ($C_1$–$C_6$)alkyl, 13 NH—CO—$OR^{12}$, and —$NR^{10}R^{11}$; $R^5$ is selected from halo, cyano, and ($C_1$–$C_6$) alkyl; $R^1$ and $R^2$ are independently selected from ($C_1$–$C_6$) alkyl; X and Y are H; and Z is chloro.

Because of their outstanding fungicidal activity and selectivity the most preferred compounds of formula I are those wherein: $R^3$ is selected from chloro, bromo, CN, and —CH=NOCH3; $R^4$ is selected from H, —NH2, CN, and —CH3; $R^5$ is selected from chloro, bromo, CN, and —CH3; $R^1$ is methyl; $R^2$ is ethyl; X and Y are H; and Z is chloro.

This invention also provides fungicidal compounds of formula I.

In addition, this invention provides a process for preparing compounds of formula I, comprising the steps of:
a. reacting a protonated amino acid ester of the formula:

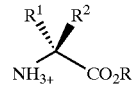

wherein $R^1$ and $R^2$ are different and are independently selected from H, ($C_1$–$C_6$)alkyl, ($C_2$–$C_6$)alkenyl, ($C_2$–$C_6$) alkynyl, and halo($C_1$–$C_6$)alkyl and $R^2$ is stereochemically larger than $R^1$,and R is selected from ($C_1$–$C_6$)alkyl, with an acyl chloride of the formula:

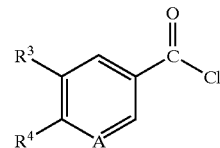

wherein A is selected from N and C-$R^5$ and $R^3$, $R^4$, and $R^5$ are independently selected from H, halo, ($C_1$–$C_6$)alkyl, ($C_2$–$C_6$)alkenyl, ($C_2$–$C_6$)alkynyl, halo($C_1$–$C_6$)alkyl, (C 1-C6)alkoxy, halo($C_1$–$C_6$)alkoxy, cyano, nitro, —$CR^6$= $NOR^7$, —$NR^8R^9$, —$CONR^{10}R^{1}$1, and —NH-CO-$OR^{12}$ wherein $R^6$ is selected from H, ($C^1$–$C^6$)alkyl, ($C_2$–$C_6$) alkenyl, and ($C^2$–$C^6$)alkynyl, $R^7$ is selected from H, ($C_1$–$C_6$) alkyl, ($C_2$–$C_6$)alkenyl, ($C^2$–$C^6$)alkynyl, and ($C_1$–$C_6$) alkylcarbonyl, $R^8$ and $R^9$ are independently selected from H, ($C_1$–$C_6$)alkyl, and ($C_1$–$C_6$)alkylcarbonyl, $R^{10}$ and $R^{11}$ are independently selected from H and ($C_1$–$C_6$)alkyl; and $R^{12}$ is selected from H, $(C_1-C_6)$alkyl, $(C_2-C_6)$alkenyl, and $(C_2-C_6)$alkynyl; to produce a benzamide-ester of the formula:

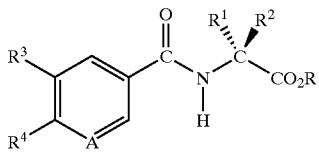

b. hydrolyzing the ester moiety of the benzamide-ester to produce a benzamide-acid of the formula:

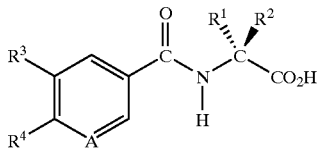

c. cyclizing the benzamide-acid to produce an oxazolinone of the formula:

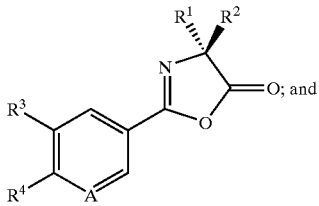

d. forming the c ompound of formula I by ring opening the oxazolinone.

The protonated amino acid ester may be prepared using standard esterification procedures such as treatment of the corresponding amino acid with an alcohol under acidic conditions. We have found that methanol is the preferred alcohol because of the ease of removal of a methyl group during the hydrolyzing step.

In a similar manner, the hydrolyzing step is conducted using standard conditions. Base catalyzed hydrolysis using sodium hydroxide as the base is preferred. The only limitations to the reaction conditions used in the hydrolyzing step are that the conditions must be sufficiently selective so that the ester bond is hydrolyzed but the amide bond is not. Strong base catalysts must be avoided when $R^1$ or $R^2$ is hydrogen to eliminate side reactions resulting from abstraction of the hydrogens.

The oxazolinone is produced in the cyclization step by dehydration of the benzamide-acid. Such dehydrations may be conducted using a variety of dehydrating agents such as acetic anhydride at elevated temperatures (90°–100° C.) phosphorous oxychloride, phosphorous pentachloride, and ethyl hloroformate/triethylamine. Mild dehydrating agents such as acetic anhydride are preferred because they are easily removed and side reactions are avoided.

Ring opening of the oxazolinone to form the compound of formula I may be conducted in a single or in multiple steps. An example of a single step ring opening is treating the oxazolinone with chloromethyllithium which produces the compound of formula I wherein X and Y are H and Z is Cl. An example of a multiple step ring opening is treating the oxazolinone first with methyllithium to form the compound of formula I wherein X, Y, and Z are all H, chlorinating the ketone to produce a mixture of compounds of formula I wherein one or two of X, Y, and Z are Cl and the remaining are H, followed by selective removal of one chlorine atom from any compound in which two of X, Y, and Z are Cl to give a compound of formula I wherein two of X, Y, and Z are H and the remaining is Cl. The removal of one chlorine atom may be accomplished by hydrogenation of the dichloro compound in the presence of a catalyst such as palladium.

This same process may also be employed to produce a racemic mixture of R and S isomers of the compound of formula I by utilizing a racemic mixture of the R and S isomers of the protonated amino acid ester in the first step.

Compositions containing compounds of formula I and an agronomically acceptable carrier are useful in controlling a broad spectrum of phytopathogenic fungi such as those of the classes Oomycetes, Deuteromycetes, and Ascomycetes.

The compositions and compounds of the present invention (compounds of formula I) are useful for the control of phytopathogenic fungi on crops and may be used as seed protectants, soil fungicides and/or foliar fungicides. As a seed protectant, a compound of the present invention is coated on seed at a dosage rate of about 5 grams (g) compound per 50 kilograms (kg) seed to about 250 g compound per 50 kg seed. As a soil fungicide, a compound of the present invention can be incorporated in the soil or applied to the surface of the soil at a dosage rate of about 0.25 kg compound per hectare to about 10 kg compound per hectare and preferably at a rate of about 0.5 kg compound per hectare to about 2.5 kg compound per hectare.

The compositions and compounds of the present invention can be applied to plant foliage as fungicidal sprays by methods commonly employed, such as conventional high-gallonage hydraulic sprays, low-gallonage sprays, air-blast, aerial sprays and dusts. While the dilution and rate of application will depend upon the type of equipment employed, the method and frequency of application desired and diseases to be controlled, the effective amount is typically from about 0.005 kg compound per hectare to about 1.0 kg compound per hectare, preferably from about 0.05 kg compound per hectare to about 0.5 kg compound per hectare and more preferably from about 0.0625 kg compound per hectare to about 0.25 kg compound per hectare.

For the above disclosed purposes these compounds can be used in the pure form, also known as technical in the art, as prepared, or as solutions or as formulations. The compounds are usually provided with a carrier or are formulated so as to render them suitable for subsequent use as fungicides. For example, the compounds can be formulated as wettable powders, dry powders, emulsifiable concentrates, dusts, granular formulations, aerosols, or flowable emulsion concentrates. In such formulations, the compounds are extended with a liquid or solid carrier and, when dried, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in McCutcheon's Emulsifiers and Detergents, McCutcheon's Emulsifiers and Detergents/Functional Materials and McCutcheon's Functional Materials all published annually by McCutcheon Division of MC Publishing Company (N.J.).

In general, the compounds utilized in this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5% to 50%.

For the preparation of emulsifiable concentrates, the compounds used in the invention can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75%. Wettable powders suitable for spraying, can be prepared by admixing the compound with a finely divided solid or mixture of solids, such as clays, inorganic silicates, inorganic carbonates, and silicas and incorporating wetting agents, sticking agents, and/or dispersing agents in such mixtures. The concentration of active ingredients in such formulations is usually in the range of 20% to 98%, preferably 40% to 75%.

Dusts are prepared by mixing the compounds of the present invention salts and complexes thereof with finely divided inert solids which can be organic or inorganic in nature. Inert materials useful for this purpose include botanical flours, silicas, silicates, carbonates and clays. One convenient method of preparing a dust is to dilute a wettable powder with a finely divided carrier. Dust concentrations containing 20% to 80% of the active ingredient are commonly made and are subsequently diluted to 1% to 10% use concentration.

The compounds of the present invention can also be utilized in combination with other fungicides such as, for example, those disclosed in U. S. Pat. No. 5,304,572 (column 3, line 30 to column 4, line 52) as well as acylalanines such as , furalaxyl, cyprofuram, ofurace, benalaxyl, and oxadixyl;, fluazinam, flumetover, phenylbenzamide derivatives such as those disclosed in EP 578586 A1, amino acid derivatives such as valine derivatives disclosed in EP 550788 A1, methoxyacrylates such as methyl (E)-2-(2-(6-(2-cyanophenoxy)pyrimidin-4-yloxy)phenyl)-3-methoxyacrylate; benzo(1,2,3)thiadiazole-7-carbothioic acid S-methyl ester: propamocarb; imazalil; carbendazim; myclobutanil; fenbuconazole; tridemorph; pyrazophos; fenarimol; fenpiclonil; pyrimethanil; and tin fungicides. Those skilled in the art will recognize that mixtures of the respective compositions and compounds of the present invention with other fungicidally active compounds may provide advantages such as a broader spectrum of antifungal activity than the respective compositions and compounds of the present invention alone.

In a similar manner, the compositions and compounds of this invention may be applied in combination with one or more insecticides such as those disclosed in U. S. Pat. No. 5,075,471 (columns 14 and 15). Again, those skilled in the art will recognize that mixtures of the respective compositions and compounds of the present invention with insecticidally active compounds may provide advantages such as fewer total applications than if the fungicides and insecticides are applied separately.

The following examples describe in detail some of the embodiments of this invention.

Methods of Preparation
Preparation of racemic isovaline [(R.S) 2-amino-2-methylbutanoic acid]. The preparation of this compound was carried out by a modified procedure from Chirality (1992) 4, 302–7.

A 2-liter stainless steel autoclave containing 5-ethyl-5-methylhydantoin (Frinton Labs) (100.0 g, 0.70 mole), barium hydroxide octahydrate (440 g, 1.395 mole) and deionized water (1.25 L) was sealed and heated to 175° C. for 15 hours. The cooled reaction mixture was filtered through diatomaceous earth (Celite). The resulting white cake was washed thoroughly with deionized water. The combined aqueous filtrate and water washings were treated with carbon dioxide gas (from 120 g of dry ice). The solid formed was separated by filtration and the clear aqueous solution was concentrated in the rotary evaporator until the wet solids coated the sides of the flask. The resulting suspension was triturated with a mixture of 1:1 acetone:ethanol (300 ml) to afford a white solid that after drying yielded 71.5 g (87.3%) of the expected racemic isovaline.

Preparation of N-chloroacetyl isovaline. Procedure adapted from J. Amer. Chem. Soc. 4701 (1952).

To a well-stirred mixture chilled to 0° C. to 5° C. (ice bath) of racemic isovaline ((R,S) 2-amino-2-methylbutanoic acid) (350 g, 2.99 mole) and 2N aqueous sodium hydroxide (1.5 L) were added simultaneously chloroacetyl chloride (373 g, 3.31 mole) and 2N aqueous sodium hydroxide (1,718 ml, 3.44 mole) over 1.5 hours . The base was added at such a rate as to keep the reaction mixture basic at all times. The reaction mixture was warmed up to room temperature, treated with concentrated aqueous hydrochloric acid until acidic to litmus paper. A white solid formed which was separated by filtration and dried to yield 454 g (78.5%) of the expected racemic N-chloroacetylisovaline ((R,S) 2-chloroacetamido-2-methylbutanoic acid).

Enzymatic resolution of racemic N-chloroacetylisovaline [(R.S) 2-chloroacetamido-2-methylbutanoic acid]. Adapted from J. Amer. Chem. Soc. 4701 (1952) and Chemistry of Amino Acids Volume 3 page 2575. John Wiley and Sons Edited by J. P. Greensteins and M. Winitz.

Racemic N-chloroacetylisovaline ((R,S) 2-chloroacetamido-2-methylbutanoic acid) (120 g, 0.62 mole) was suspended in purified deionized water (1 L) and brought into solution by the addition of 2N aqueous sodium hydroxide to a pH of 7.5. Acylase I powder 75% (Sigma Chemicals Catalog Number A-3010) (1 g) was added and the pH was adjusted to 7.5. The resulting mixture was digested at 38° C. for 72 to 96 hours. The pH of the reaction mixture was adjusted to 5, and the resulting mixture stirred at 95° C. for approximately 2 hours. The aqueous mixture was filtered yielding a clear, slightly yellow solution. A total of 5 batches were run under the same conditions. All the batches were combined and divided in three. Each of these three batches was poured into a Dowex 50 (H+) column (1.75 L of wet resin) and washed with water until the pH of the eluate was greater than 5. The eluate was concentrated yielding (R)-N-chloroacetylisovaline. The (S)-isovaline on the Dowex 50 resin column was eluted with 2.5N aqueous hydrochloric acid (approximately 4 L). The combined acidic eluate was concentrated in vacuo . The resulting white solid was vacuum dried yielding a total of 355 g of a mixture of (S)-isovaline hydrochloride and sodium chloride used as such in the next step.

Preparation of (S)-isovaline methyl ester hydrochloride [Methyl (S)-2-amino-2-methylbutanoate]

To a well-stirred suspension of the previous mixture of (S)-isovaline hydrochloride and sodium chloride in methanol (3 L) was slowly added thionyl chloride (373 g, 3.13 mole). After the addition was complete the reaction mixture was refluxed for 3 hours. The resulting mixture was cooled to room temperature and filtered. The resulting white filter cake was washed several times with methanol. The combined methanol filtrate and washings were concentrated using a rotary evaporator. Toluene was added to the resulting crude residue and then removed using the rotary evaporator yielding 187 g of the expected (S)-isovaline methyl ester hydrochloride.

Preparation of (S)-N-(3.5-dichloro-4-methylbenzoate) isovaline methyl ester

In a 5-liter round-bottomed flask were placed the previously prepared (S)-isovaline methyl ester hydrochloride (280 g, 1.67 mole), 3,5-dichloro-4-methylbenzoyl chloride (381 g, 1.705 mole) and methylene chloride (2.2 L). The mixture was cooled to 0° C. To the resulting cooled (0° C.) mixture was added slowly triethylamine (540 ml) keeping the reaction mixture at 0 ° C. When the addition was complete the reaction mixture was stirred at 0° C. for 30 minutes and then allowed to warm up to room temperature. The reaction mixture was washed sequentially with water, 2% aqueous hydrochloric acid, water, saturated aqueous sodium bicarbonate and finally brine. The organic layer was dried over anhydrous magnesium sulfate and solvent eliminated using a rotary evaporator yielding 505.9 g of the expected (S) N-(3,5-dichloro-4-methylbenzoate) isovaline methyl ester which was used as such in the next step.

Preparation of (S)-N-(3.5-dichloro-4-methylbenzoate) isovaline

To a mixture of the previously prepared (S)-N-(3,5-dichloro-4-methylbenzoate) isovaline methyl ester (315 g) and methanol (3 L) at 55 ° C was added slowly aqueous sodium hydroxide (10% solution, 869 g, 2.17 mole). When the addition was complete the reaction mixture was refluxed for 1 hour. The reaction mixture was cooled to room temperature and the solvent eliminated using a rotary evaporator. The crude reaction product was taken up in water, the resulting aqueous solution was washed 3 times with ethyl acetate, and made acidic with concentrated aqueous hydrochloric acid. The product settled first as an oil which quickly solidified. The solids were separated by filtration, washed several times with water and dried in a vacuum oven yielding 279 g of the expected (S) N-(3,5-dichloro-4-methylbenzoate) isovaline which was used as such in the next step.

Preparation of (S)-2-(3.5-dichloro-4-methylbenzoyl)-4-ethyl-4-methyl-1,3-oxazol-5-one.

A mixture of the previously prepared (S)-N-(3,5-dichloro-4-methylbenzoate) isovaline (279 g, 0.917 mole) and acetic anhydride (1.25 L) was refluxed for 1 hour. The reaction mixture was cooled to room temperature and the solvent was eliminated in the rotary evaporator yielding a thick oily residue. This residue was treated with xylene and the solvent was eliminated using a rotary evaporator. The resulting crude product was dried in a vacuum oven yielding 275.5 g of the expected (S)-2-(3,5-dichloro-4-methylbenzoyl)-4-ethyl-4-methyl-1,3-oxazol-5-one as an oil that quickly solidified. The compound was used as such in the next step.

Preparation of (S)-N-(1-ethyl-1-methyl-2-oxopropyl)-3,5-dichloro-4-515 methylbenzamide In a 3-liter four-necked round-bottomed flask equipped with mechanical stirrer, condenser with nitrogen inlet on top, thermometer, and addition funnel were placed the previously prepared 2-(3,5-dichloro-4-methylbenzoyl)-4-ethyl-4-methyl-1,3-oxazol-5-one (107 g, 0.374 mole) and dry tetrahydrofuran (1.4 L). To the resulting mixture cooled down to −70° C. was added slowly dropwise methyllithium (1.4 M solution, 280 ml, 0.392 mole) over 20 minutes period. After the addition was complete the reaction mixture was warmed up to room temperature and poured into a saturated aqueous solution of ammonium chloride. The organic phase was separated and the aqueous layer was extracted three times with ethyl acetate. The combined organic layers were dried over anhydrous magnesium sulfate and the solvent eliminated in the rotary evaporator yielding 117.3 g of the expected (S)-N-(1-ethyl-1-methyl-2-oxopropyl)-3,5-dichloro-4-methylbenzamide as a thick oil.

Preparation of (S)-N-(3-chloro- 1-ethyl- 1-methyl-2-oxopropyl)-3.5-dichloro-4-methylbenzamide and (S)-N-(3.3-dichloro- 1-ethyl- 1-methyl-2-oxopropyl)-3.5-dichloro-4-methylbenzamide In a 2-liter four-necked round-bottomed flask equipped with mechanical stirrer, condenser with inlet on top connected to an acid scrubber, thermometer, and gas inlet tube were placed the previously prepared (S)-N-(1-ethyl-1-methyl-2-oxopropyl)-3,5-dichloro-4-methylbenzamide (115 g, 0.38 mole) and glacial acetic acid (1 L). The resulting mixture was warmed up to 60 ° C. and chlorine gas was admitted into the well-stirred reaction mixture. Chlorine was bubbled in until thin layer chromatography showed no more starting material. The reaction mixture was cooled down to room temperature and the solvent eliminated in the rotary evaporator yielding the crude product. This residue was triturated with hexane and filtered yielding 121.2 g of a mixture of (S)-N-(3-chloro-1-ethyl-1-methyl-2-oxopropyl)-3,5-dichloro-4-methylbenzamide and (S)-N-(3,3-dichloro-1-ethyl- 1-methyl-2-oxopropyl)-3,5-dichloro-4-methylbenzamide which was used as such in the next step.

Preparation of (S)-N-(3-chloro-1-ethyl-1-methyl-2-oxopropyl)-3.5-dichloro-4-methylbenzamide The mixture (87 g) prepared in the previous step, 1.35 L of ethanol and 800 mg of 5% palladium over charcoal were placed in a hydrogenation bottle and hydrogenated in a Parr apparatus (50 psi, room temperature) for 3 hours. The reaction mixture was filtered through Celite and the solvent eliminated under reduced pressure, to yield a crude product. The crude product was triturated with hexane and filtered yielding after drying 56.6 g of the expected (S)-N-(3-chloro-1-ethyl- 1-methyl-2-oxopropyl)-3,5-dichloro-4-methylbenzamide methylbenzamide (mp. 154–155° C., $[\alpha]_D$=−4.1 in ethanol).

Preparation of (R)-isovaline methyl ester

In a 2-liter round-bottomed flask equipped with a condenser and a magnetic stirrer were placed 70 g of the (R)-N-chloroacetylisovaline obtained from the enzymatic resolution of racemic N-chloroacetylisovaline, 696 ml of water, and 696 ml of concentrated hydrochloric acid. The resulting mixture was heated at reflux for 2.25 hours. The mixture was then cooled to room temperature and the solvent was removed using rotary evaporation yielding a solid residue. the residue was washed with dry acetone and then dried in a vacuum oven at 40° C. yielding a crude product. The crude product was esterified with methanol using the above-described procedure for preparation of (S)-isovaline methyl ester hydrochloride to give 47.52 g of the corresponding (R)-isovaline methyl ester hydrochloride.

The (R)-isovaline methyl ester hydrochloride may be converted to (R)-N-(3-chloro-1-ethyl- 1-methyl-2-oxopropyl)-3,5-dichloro-4-methylbenzamide (mp. 155.5–156° C., $[\alpha]_D$=+4.14 in ethanol) using the above-described sequence for preparation of the (S)-enantiomer.

Biological Evaluation

In the following examples two different compounds were tested as individual enantiomers and as racemic mixtures. The compounds were evaluated as follows:

Compound 1 A=C-Cl, $R^1$ /$R^2$=methyl/ethyl; $R^3$=Cl, $R^4$=methyl; X and Y=H; and Z=Cl Compound 2A=C-Cl, $R^1$ /$R^2$=methyl/ethyl; $R^3$=Cl, $R^4$=H; X and Y=H; and Z=Cl Fungitoxicity assay against *Pythium ultimum*

A series of dilutions of each test compound was prepared in dimethyl sulfoxide, and 0.1 ml of each dilution was added to 19.9 ml of a liquid asparagine-sucrose broth (Erwin, D. C. and Katznelson, K., 1971, Can. J. Microbiol. 7, 15) in 9 cm diameter petri dishes to give the desired concentrations of test compound in the medium. Each plate was inoculated with a mycelial plug, 7 mm in diameter, taken from the growing edge of a culture of Pythium ultimum grown on potato dextrose agar. Two replicate plates were used for each treatment. The increase in mycelial dry weight was determined after growth for 48 hours at 25° C. with shaking on a gyrotary shaker at 60 rpm. Pythium EC50 values were calculated from dose response curves. As used herein, the terminology "EC50" means the concentration of test compound required to inhibit growth by 50% as compared to a control lacking the test compound.

Fungitoxicity assay against Phytophthora capsici

The procedure described above for Pythium ultimum was used except that the mycelial plugs used for inoculation were taken from the growing edge of cultures of Phytophthora capsici grown on V-8 juice agar, pH 7.0, containing 200 ml V-8 juice, 4 g $CaCO_3$, and 20 g agar per liter, and the increase in mycelial dry weight was determined after growth for 96 h.

Fungitoxicity assay against Botrytis cinerea

A series of dilutions of each test compound was prepared in dimethyl sulfoxide and 125 microliters (A1) of each dilution was added to 25 ml of molten potato dextrose agar to give the desired concentrations of test compound. The mixtures were poured immediately into 9 cm diameter petri dishes. Each plate was inoculated with a 7 mm diameter mycelial plug taken from the growing edge of a 5 day old culture of B. cinerea grown on potato dextrose agar. Plates were incubated at 25° C. for 48 hours, then the colony diameters were measured and EC50 values calculated from dose-response curves.

In order to compare the activity of individual isomers with that of the corresponding racemic mixture, the relative effectiveness of each compound was calculated. As used herein, relative effectiveness means the EC50 value for a racemic mixture of the particular compound divided by the EC50 value for one enantiomer. The relative effectiveness of the racemic mixture itself is 1.0. Results are presented in the following table.

| Compound | Relative Effectiveness against | | |
| --- | --- | --- | --- |
| | Pythium ultimum | Phytophthora capsici | Botrytis cinerea |
| 1, racemate | 1.00 | 1.00 | 1.00 |
| 1, S enantiomer | 2.18 | 2.13 | 2.03 |
| 1, R enantiomer | 0.037 | 0.0072 | <0.076 |
| 2, racemate | 1.00 | | 1.00 |
| 2, S enantiomer | 2.68 | | 1.85 |
| 2, R enantiomer | 0.055 | | 0.17 |

Based upon these results, one skilled in the art would expect that intermediate mixtures of racemate and S enantiomer would have intermediate effectiveness. That is, for mixtures of the racemate and S enantiomer of compound 1 for example, the expected effectiveness against Pythium ultimum would be as follows:

| % S in the Mixture | Relative Effectiveness |
| --- | --- |
| 50 | 1.000 |
| 60 | 1.236 |
| 70 | 1.472 |
| 80 | 1.708 |
| 90 | 1.944 |
| 100 | 2.180 |

Compounds were tested for fungicidal activity against Phytophthora infestans, Plasmopara viticola and Botrytis cinerea according to the procedures set forth below.

Tomato Late Blight (TLB)

Spore suspensions, obtained from 1–2 week old Phytophthora infestans cultures grown on V8 juice agar, were used to inoculate tomato seedlings that were about two weeks old. A DeVilbiss atomizer was used to apply the spores to the fungicide-treated foliage. The plants were kept in a humidity cabinet at 100% relative humidity for 24 hours, and then placed in a controlled temperature chamber at 25° C. for disease development. Disease evaluations were made 6 days after inoculation and were recorded as "percent disease control", i.e., the relative efficacy of the test compound compared to no treatment, with 100% disease control indicating that the plants were observed to be free of disease.

Tomato Late Blight-Curative (TLC)

The curavite properties of the test compounds were evaluated using the same procedure as that set forth above in the section entitled "TOMATO LATE BLIGHT", except that the test compound was applied to the plants two days after inoculation with the pathogen.

Grape Downy Mildew (GDM)

Cultures of Plasmopara viticola were maintained on grape seedlings derived from tissue culture. Leaves with sporulating mildew were rinsed in water to obtain the desired concentration of spores. A DeVilbiss atomizer was used to apply a suspension of spores to fungicide-treated lower leaves of the grape plants. The plants were kept in a humidity cabinet at 100% relative humidity for 24 hours and then placed in a controlled temperature chamber at 25° C. for 7–8 days before scoring. Disease evaluations were recorded as percent disease control.

Grape Downy Mildew-Curative (GDC)

The curative properties of the test compounds were evaluated using the same procedure as that set forth above in the section entitled "GRAPE DOWNY MILDEW", except that the test compound was applied to the plants two days after inoculation with the pathogen.

Gray Mold on Tomato-Curative (BOC)

Botrytis cinerea cultures were maintained on potato dextrose agar. A dextrose solution was used to wash spores from sporulating cultures. A DeVilbiss atomizer was used to apply the resulting spore suspension to tomato plants. The plants were placed in a humidity cabinet at 100% relative humidity, and the test compound was applied to the plants after 2 days. The plants were returned to the humidity cabinet for a further 3–5 days before scoring. Disease evaluations were recorded as percent disease control.

Fungicidal activity against the above discussed phytopathogenic fungi is set forth in the following table expressed as percent disease control.

| Compound | Rate* | TLB | GDM | TLC | GDC | BOC |
|---|---|---|---|---|---|---|
| 1, racemate | 300 | 95 | 100 | 95 | 90 | 90 |
| | 75 | 100 | 100 | 90 | 50 | 75 |
| | 19 | 85 | 99 | 80 | 50 | 50 |
| 1, S enantiomer | 300 | 100 | 100 | 95 | 99 | 95 |
| | 75 | 100 | 100 | 99 | 90 | 90 |
| | 19 | 90 | 99 | 90 | 75 | 75 |
| 1, R enantiomer | 300 | 75 | 0 | 0 | 0 | 0 |
| | 75 | 50 | 0 | 0 | 0 | 0 |
| | 19 | 25 | 0 | 0 | 0 | 0 |

*Application rate is expressed in parts per million (ppm)

We claim:

1. A composition, comprising:

a. one or more compounds of formula I, with the stereochemistry depicted:

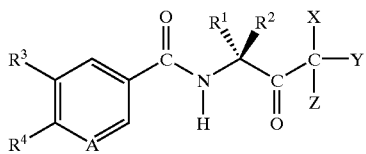

I wherein:

1. A is C-R5;
2. $R^1$ and $R^2$ are different and are independently selected from H, $(C_1-C_6)$alkyl, $(C_2-C_6)$alkenyl, $(C_2-C_6)$ alkynyl, and halo$(C_1-C_6)$alkyl and $R^2$ is stereochemically larger than $R^1$;
3. $R^3$, $R^4$, and RG) are independently selected from H, halo, $(C_1-C_6)$alkyl, $(C_2-C_6)$alkenyl, $(C_1-C_6)$alkynyl, halo$(C^1-C^6)$alkyl, $(C_1-C_6)$alkoxy, halo$(C^1-C^6)$alkoxy, cyano, nitro, $-CR^6=NOR^7$, $-NR^8R^9$, $CONR^1OR^1$ 1, and $-NH-CO-OR^{12}$ wherein $R^6$ is selected from H, $(C^1-C^6)$alkyl, $(C_2-C_6)$alkenyl, and $(C2A-C6)$alkynyl, $R^7$ is selected from H, $(C_1-C_6)$alkyl, $(C_2-C_6)$alkenyl, $(C_2-C_6)$alkynyl, and $(C_1-C_6)$alkylcarbonyl, $R^8$ and $R^9$ are independently selected from H, $(C_1-C_6)$alkyl, and $(C^1-C^6)$alkylcarbonyl, $R^{10}$and $R^{11}$ are independently seleceted from H and $(C_1-C_6)$alkyl; and $R^{12}$ is seleceted from H, $(C^1-C^6)$alkyl, $(C_2-C_6)$alkenyl, and $(C_2-C_6)$ alkynyl;
4. X, Y, and Z are independently selected from H, halo, cyano, thiocyano, isothiocyano, and $(C_1-C_4)$ alkylsulfonyloxy; provided that X, Y, and Z are not all H; and b. an agronomically acceptable carrier; wherein the composition is predominantly free of the compound of formula I wherein $R^1$ is stereochemically larger than $R^2$;.

2. The composition of claim 1 wherein $R^3$ is selected from halo, cyano,nitro, and $-CH=NOCH3$; $R^4$ is selected from H, halo, cyano, $(C^1-C^6)$alkyl, $-NH-CO-OR^{12}$, and $-NR^{10}R^{11}$; $R^5$ is selected from halo, cyano, and $(C_1-C_6)$ alkyl; $R^1$ and $R^2$ are independently selected from $(C_1-C_6)$ alkyl; X and Y are H; and Z is chloro.

3. The composition of claim 1 wherein $R^3$ is selected from chloro, bromo, cyano and $-CH=NOCH3$; $R^4$ is selected from H, $-NH2$, cyano, and $-CH3$; $R^5$ is selected from chloro, bromo, cyano, and $-CH3$; $R^1$ is methyl; $R^2$ is ethyl; X and Y are H; and Z is chloro.

4. A process for preparing a compound of the formula:

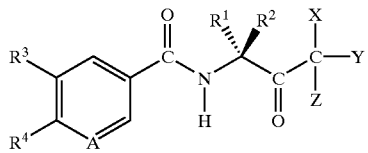

with the stereochemistry depicted, comprising the steps of:

a. reacting a protonated amino acid ester of the formula:

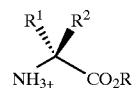

wherein $R^1$ and $R^2$ are different and are independently selected from H, $(C_1-C_6)$alkyl, $(C_2-C_6)$alkenyl, $(C_2-C_6)$ alkynyl, and halo$(C_1-C_6)$alkyl and R is selected from $(C_1-C_6)$alkyl, with an acyl chloride of the formula:

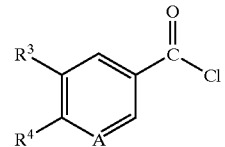

wherein A is selected from N and C-$R^5$ and $R^3$, $R^4$, and $R^5$ are independently selected from H, halo, $(C_1-C_6)$alkyl, $(C_2-C_6)$alkenyl, (C2-C6)alkynyl, halo(CI-C6)alkyl, $(C^1-C^6)$alkoxy, halo$(C^1-C^6)$alkoxy, cyano, nitro, $-CR^6=NOR^7$, $-NR^8R^9$, $-CONR^1OR^{11}$, and $-NH-CO-OR^{12}$ wherein $R^6$ is selected from H, $(C_1-C_6)$alkyl, $(C_2-C_6)$ alkenyl, and $(C_2-C_6)$alkynyl, $R^7$ is selected from H, $(C_1-C_6)$ alkyl, $(C_2-C_6)$alkenyl, $(C_2-C_6)$alkynyl, and $(C_1-C_6)$ alkylcarbonyl, $R^8$ and $R^9$ are independently selected from H, (C1-C6)alkyl, and $(C_1-C_6)$alkylcarbonyl, $R^{10}$and $R^1$ are independently selected from H and $(C_1-C_6)$alkyl; and $R^{12}$ is selected from H, (C1-C6)alkyl, $(C_2-C_6)$alkenyl, and $(C_2-C_6)$alkynyl; to produce a benzamide-ester of the formula:

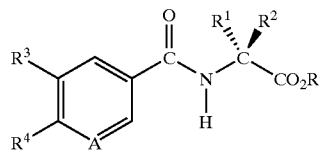

b. hydrolyzing the ester moiety of the benzamide-ester to produce a benzamide-acid of the formula:

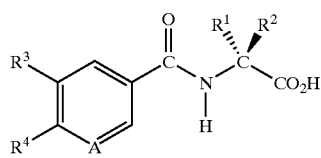

c. cyclizing the benzamide-acid to produce an oxazolinone of the formula:

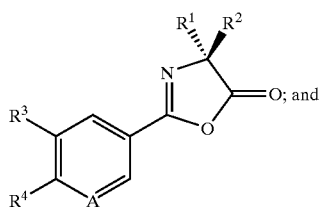

d. forming the compound by ring opening the oxazolinone.

5. The process of claim 4 wherein the forming step comprises:
   a. treating the oxazolinone with an organometallic agent;
   b. halogenating the resulting ketone; and
   c. hydrogenating of the dihaloketone.

6. The process of claim 4 wherein the organometallic agent is chloromethyllithium.

7. A method for controlling phytopathological fungi comprising applying a fungicidally effective amount of the composition of claim 1 to plant foliage, plant seed, or plant growth medium.

8. The composition of claim 1 further comprising one or more pesticides selected from fungicides and insecticides.

9. A process for preparing a racemic mixture of the (R) and (S) enantiomers of a compound of the formula:

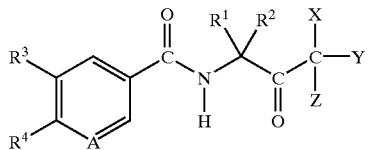

comprising the steps of
   a. reacting a protonated amino acid ester of the formula:

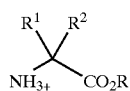

wherein $R^1$ and $R^2$ are different and are independently selected from H, $(C_1-C_6)$alkyl, $(C_2-C_6)$alkenyl, $(C_2-C_6)$alkynyl, and halo$(C_1-C_6)$alkyl and R is selected from $(C_1-C_6)$alkyl, with an acyl chloride of the formula:

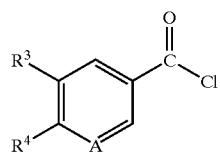

wherein A is selected from N and C-$R^5$ and $R^3$, $R^4$, and $R^5$ are independently selected from H, halo, $(C_1-C_6)$ alkyl, $(C_2-C_6)$alkenyl, $(C_2-C_6)$alkynyl, halo$(C_1-C_6)$ alkyl, $(C_1-C_6)$alkoxy, halo$(C_1-C_6)$alkoxy, cyano, nitro, —$CR^6$=$NOR^7$, —$NR^8R^9$, —$CONR^{10}R^{11}$, and —NH-CO-$OR^{12}$ wherein $R^6$ is selected from H, $(C^1-C^6)$alkyl, $(C_2-C_6)$alkenyl, and $(C_2-C_6)$alkynyl, $R^7$ is selected from H, $(C^1-C^6)$alkyl, $(C_2-C_6)$alkenyl, $(C_2-C_6)$ alkynyl, and $(C^1-C^6)$alkylcarbonyl, $R^8$ and $R^9$ are independently selected from H, $(C_1-C_6)$alkyl, and $(C^1-C^6)$alkylcarbonyl, $R^{10}$ and $R^1$ 1 are independently selected from H and $(C^1-C^6)$alkyl; and $R^{12}$ is selected from H, $(C_1-C_6)$alkyl, $(C_2-C_6)$alkenyl, and $(C_2-C_6)$ alkynyl; to produce a benzamide-ester of the formula:

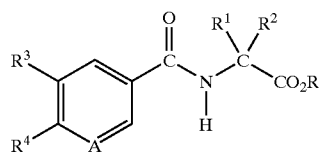

b. hydrolyzing the ester moiety of the benzamide-ester to produce a benzamide-acid of the formula:

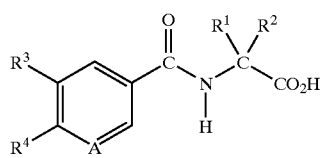

c. cyclizing the benzamide-acid to produce an oxazolinone of the formula:

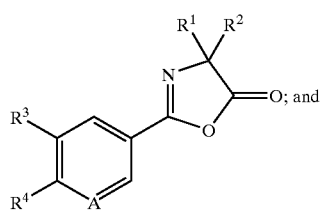

d. forming the racemic mixture by ring opening the oxazolinone.

10. The process of claim 9 wherein the forming step comprises:
   a. treating the oxazolinone with an organometallic agent;
   b. halogenating the resulting ketone; and
   C. hydrogenating of the dihaloketone.

11. The process of claim 10 wherein the organometallic agent is chloromethyllithium.

* * * * *

UNITED STATES PATENT AND TRADEMARK OFFICE
CERTIFICATE OF CORRECTION

PATENT NO. : 6,566,403 B1
DATED : May 20, 2003
INVENTOR(S) : Enrique L. Michelotti et al.

It is certified that error appears in the above-identified patent and that said Letters Patent is hereby corrected as shown below:

Column 11,
Line 30, should read -- A is $C-R^5$; -- rather than "A is C-R5;"
Lines 36-39, should read -- $R^3$, $R^4$, and $R^5$) are independently selected from H, halo, $(C_1-C_6)$ alkyl, $(C_2-C_6)$alkenyl, $(C_2-C_6)$alkynyl, halo$(C_1-C_6)$alkyl, $(C_1-C_6)$alkoxy, halo $(C_1-C_6)$alkoxy, cyano, nitro, —$CR^6=NOR^7$, —$NR^8R^9$, —$CONR^{10}OR^{11}$, -- rather than "$R^3$, $R^4$, and RG) are independently selected from H, halo, $(C_1-C_6)$alkyl, $(C_2-C_6)$ alkenyl, $(C_1-C_6)$alkynyl, halo$(C^1-C^6)$alkyl, $(C_1-C_6)$alkoxy, halo$(C^1-C^6)$alkoxy, cyano, nitro, —$CR^6=NOR^7$, —$NR^8R^9$, $CONR^1OR^1$1,"
Line 41, should read -- $(C_1-C_6)$alkyl, $(C_2-C_6)$alkenyl, and $(C_2-C_6)$alkynyl, -- rather than "$(C^1-C^6)$alkyl, $(C_2-C_6)$alkenyl, and (C2A-C6)alkynyl,"
Line 45, should read -- $(C_1-C_6)$alkylcarbonyl, $R^{10}$ and $R^{11}$ are independently -- rather than "$(C^1-C^6)$alkylcarbonyl, $R^{10}$ and $R^{11}$ are independently"
Lines 47-48, should read -- from H, $(C_1-C_6)$alkyl, $(C_2-C_6)$alkenyl, and $(C_2-C_6)$alkynyl; and -- rather than "from H, $(C^1-C^6)$alkyl, $(C_2-C_6)$alkenyl, and $(C_2-C_6)$alkynyl;"
Lines 58-59, should read -- halo, cyano, nitro, and —$CH=NOCH_3$; $R^4$ is selected from H, halo, cyano, $(C_1-C_6)$alkyl, —$NH-CO-OR^{12}$, and -- rather than "halo, cyano, nitro, and —CH=NOCH3; $R^4$ is selected from H, halo, cyano, $(C^1-C^6)$alkyl, —NH-CO-OR$^{12}$, and"
Lines 64-65, should read -- chloro, bromo, cyano and —$CH=NOCH_3$; $R^4$ is selected from H, —$NH_2$, cyano, and —$CH_3$, $R^5$ is selected from -- rather than "chloro, bromo, cyano and —CH=NOCH3; $R^4$ is selected from H, —NH2, cyano, and —CH3, $R^5$ is selected from"

Column 12,
Lines 34-36, should read -- $(C_2-C_6)$alkenyl, $(C_2-C_6)$alkynyl, halo$(C_1-C_6)$alkyl, $(C_1-C_6)$ alkoxy, halo$(C_1-C_6)$alkoxy, cyano, nitro, —$CR^6=NOR^7$, —$NR^8R^9$, —$CONR^1OR^{11}$, and —$NH-CO-OR^{12}$ -- rather than "$(C_2-C_6)$alkenyl, (C2-C6)alkynyl, halo(C1-C6)alkyl, $(C^1-C^6)$alkoxy, halo$(C^1-C^6)$alkoxy, cyano, nitro, —$CR^6=NOR^7$, —$NR^8R^9$, —$CONR^1OR^{11}$, and —NH-CO-OR$^{12}$"
Line 42, should read -- $(C_1-C_6)$alkyl, and $(C_1-C_6)$alkylcarbonyl, $R^{10}$ and $R^{11}$ are -- rather than "(C1-C6)alkyl, and $(C_1-C_6)$alkylcarbonyl, $R^{10}$ and $R^1$1are"
Lines 44-46, should read -- selected from H, $(C_1-C_6)$alkyl, $(C_2-C_6)$alkenyl, and $(C_2-C_6)$alkynyl; to produce a benzamide-ester of the formula: -- rather than "selected from H, (C1-C6)alkyl, $(C_2-C_6)$alkenyl, and $(C_2-C_6)$alkynyl; to produce a benzamide-ester of the formula:"

UNITED STATES PATENT AND TRADEMARK OFFICE
CERTIFICATE OF CORRECTION

PATENT NO. : 6,566,403 B1
DATED : May 20, 2003
INVENTOR(S) : Enrique L. Michelotti et al.

It is certified that error appears in the above-identified patent and that said Letters Patent is hereby corrected as shown below:

<u>Column 14,</u>
Line 4, should read -- CO-OR$^{12}$ wherein R$^6$ is selected from H, (C$_1$-C$_6$)alkyl, -- rather than "CO-OR$^{12}$ wherein R$^6$ is selected from H, (C$^1$-C$^6$)alkyl,"
Line 6, should read -- from H, (C$_1$-C$_6$)alkyl, (C$_2$-C$_6$)alkenyl, (C$_2$-C$_6$) -- rather than "from H, (C$^1$-C$^6$)alkyl, (C$_2$-C$_6$)alkenyl, (C$_2$-C$_6$)"
Lines 10-11, should read -- (C$_1$-C$_6$)alkylcarbonyl, R$^{10}$ and R$^{11}$ are independently selected from H, (C$_1$-C$_6$)alkyl; and R$^{12}$ is selected -- rather than "(C$^1$-C$^6$)alkylcarbonyl, R$^{10}$ and R$^1$1 are independently selected from H, (C$_1$-C$_6$)alkyl; and R$^{12}$ is selected"
Lines 13-14, should read -- alkynyl; to produce a benzamide-ester of the formula: -- rather than "alkynyl; to produce a benzamide-ester of the formula:"

Signed and Sealed this

Twenty-third Day of September, 2003

JAMES E. ROGAN
*Director of the United States Patent and Trademark Office*